United States Patent [19]
Howard, Jr. et al.

[11] Patent Number: 5,939,198
[45] Date of Patent: Aug. 17, 1999

[54] POROUS POLYTETRAFLUORO-ETHYLENE AND PREPARATION

[75] Inventors: Edward George Howard, Jr., Hockessin; Arthur Zenker Moss, Wilmington, both of Del.

[73] Assignee: E. I. du Pont de Nemours and Company, Wilmington, Del.

[21] Appl. No.: 09/121,159

[22] Filed: Jul. 23, 1998

Related U.S. Application Data

[62] Division of application No. 08/812,987, Mar. 4, 1997, Pat. No. 5,840,775, which is a division of application No. 08/406,624, Mar. 20, 1995, Pat. No. 5,721,283, which is a continuation-in-part of application No. 08/169,461, Dec. 17, 1993, abandoned, which is a continuation-in-part of application No. 08/065,735, May 21, 1993, abandoned, which is a continuation-in-part of application No. 07/936,447, Aug. 28, 1992, abandoned, which is a continuation-in-part of application No. 07/904,244, Jun. 25, 1992, abandoned.

[51] Int. Cl.$^6$ .............................. B01D 39/14; C08J 9/14
[52] U.S. Cl. .............. 428/421; 210/500.21; 210/500.36; 210/510.1; 428/422; 428/315.5; 521/59; 521/60; 521/61; 521/63; 521/64; 521/134; 521/145
[58] Field of Search ................................... 521/59, 60, 61, 521/63, 64, 134, 145; 428/315.5, 421, 422; 210/500.21, 500.36, 510.1

[56] References Cited

U.S. PATENT DOCUMENTS

| | | | |
|---|---|---|---|
| 2,510,078 | 6/1950 | Compton et al. | |
| 2,593,582 | 4/1952 | Lontz et al. | |
| 3,664,915 | 5/1972 | Gore | |
| 3,692,153 | 9/1972 | Gore | |
| 3,953,566 | 4/1976 | Gore | 264/288 |
| 4,096,227 | 6/1978 | Gore | |
| 4,110,392 | 8/1978 | Yamazaki | 264/127 |
| 4,187,390 | 2/1980 | Gore | |
| 4,248,924 | 2/1981 | Okita | 428/212 |
| 4,360,488 | 11/1982 | Barham et al. | 264/210.1 |
| 4,385,026 | 5/1983 | Barham | 264/288.4 |
| 4,482,516 | 11/1984 | Bowman | 264/127 |
| 4,598,011 | 7/1986 | Bowman | 428/221 |
| 4,882,113 | 11/1989 | Tu et al. | 264/127 |
| 4,990,294 | 2/1991 | Yen et al. | 264/41 |
| 5,032,274 | 7/1991 | Yen et al. | |
| 5,110,527 | 5/1992 | Harada et al. | 264/127 |
| 5,721,283 | 2/1998 | Howard, Jr. et al. | 521/60 |

FOREIGN PATENT DOCUMENTS

| | | |
|---|---|---|
| 0 340 732 | 2/1989 | European Pat. Off. |
| 60-171140 | 9/1985 | Japan |
| 3-221541 | 9/1991 | Japan |

*Primary Examiner*—John M. Cooney, Jr.

[57] ABSTRACT

This invention relates to porous polyfluoroethylene (PTFE), shaped articles prepared therefrom, and to methods of preparing said articles.

9 Claims, 4 Drawing Sheets

POROUS POLYTETRAFLUORO-ETHYLENE AND PREPARATION

This is a divisional application of Ser. No.: 08/812,987, filed on Mar. 4, 1997, which is now U.S. Pat. No. 5,840,775, which is a divisional of Ser. No.: 08/406,624, filed Mar. 20, 1995, which is now U.S. Pat. No. 5,721,283, which is a continuation-in-part of Ser. No.: 08/169,461, filed on Dec. 17, 1993, which is now abandoned, which is a continuation-in-part of Ser. No. 08/065,735, filed on May 21, 1993, which is now abandoned, which is a continuation-in-part of Ser. No. 07/936,447, filed on Aug. 28, 1992, which is now abandoned, which is a continuation-in-part of Ser. No. 07/904,244, filed on Jun. 25, 1992, which is now abandoned.

FIELD OF THE INVENTION

This invention relates to porous polytetrafluoroethylene (PTFE) compositions, shaped articles made therefrom, and their preparation.

TECHNICAL BACKGROUND

U.S. Pat. Nos. 4,360,488 and 4,385,026 disclose formation of "non-draining" gels by heating PTFE with a highly fluorinated high-boiling material at a temperature close to the crystalline melting point of the polymer (330–350° C.). A solution or swollen mass containing from about 1 to about 50 weight % polymer is formed on heating, from which is recovered, on cooling, a sponge-like gel, said gel being without defined shape and retaining no "memory" of the crystallinity of the original PTFE. The gel, after removal of the fluorinated material by extraction in refluxing solvent such as Freon®-113 (bp 45.8° C.), is described as porous, and could be formed into porous shapes, e.g., into porous sheet by pressing between platens. The process appears to employ granular PTFE only and, because crystalline memory is lost during processing, the initial gels are shapeless globs which require post fabrication into shaped articles. The porous products have increased crystallinity and a partially fibrillar structure. Use as filter membranes or diaphragms for electrochemical cells is disclosed.

Microporous PTFE films and sheeting are known. U.S. Pat. No. 3,664,915 discloses uniaxially stretched film having at least 40% voids and a highly fibrillar structure. U.S. Pat. Nos. 3,953,566, 3,962,153 and 4,187,390 disclose porous PTFE films having at least 70% voids, said films consisting of nodes and fibrils wherein the nodes are at least 1000 times thicker than the fibrils. Pore size in the above films is at least 0.2 µm. Unsintered, paste-extruded PTFE film is stretched at rates of over 2000%/sec and as high as 40,000%/sec to achieve porosity, followed by sintering nder constraint at 327 to 370° C. Such stretching rates are far higher than those employed in conventional film preparation. U.S. Pat. No. 4,110,392 discloses microporous PTFE films having pore sizes as low as 0.01 µm, achieved by stretching unsintered PTFE as above, followed by sintering without constraint, then stretching a second time at high speed. Porosities of these films are 10 to 50%. Japanese Application 3-221541 discloses microporous PTFE film with pore size of 0.1 to 0.2 µm. The films are prepared by a modification of the above-described art procedures and have different film morphology and improved air permeability. However, ultrahigh stretching rates are again required. The art does not provide the means of improving porous PTFE articles by stretching at conventional rates.

U.S. Pat. No. 5,110,527 discloses porous PTFE films exhibiting pore sizes of at least 15 µm and voids of 80% and greater fabricated by a method in which a blend of PTFE resins of high and low molecular weight is paste-extruded into a sheet, stretched at temperatures below the melting point, and finally sintered while held in the stretched state by exposure to temperatures of at least 327° C.

SUMMARY OF THE INVENTION

The present invention provides for porous products made from high molecular weight PTFE, and the processes for the production thereof. The present invention provides a novel process (I) for introducing porosity into PTFE, said process comprising (a) contacting PTFE with a fluid which penetrates and swells, but does not significantly dissolve the polymer or eliminate viscoelastic memory therefrom, at a temperature in the range of about 250–400° C.; (b) cooling and separating the penetrated, swollen polymer from unabsorbed fluid, said polymer containing up to about 80% by weight of absorbed fluid, preferably up to 50% by weight of absorbed fluid; and (c) removing the absorbed fluid, to form a porous product having a single DSC melting endotherm, said endotherm being in the range of about 315° C. to 333° C. with an associated heat of fusion of at least 35 J/g. In step (a), temperatures within the range of about 250° C. to 400° C., should be sufficiently high for the selected fluid to extensively penetrate and swell the PTFE under process conditions, but low enough to avoid significant dissolution of the polymer or loss of viscoelastic memory therefrom. Preferably, the temperature is at or near the melting point of the PTFE under process conditions. Usually, this temperature is in the range of about 290° C. to 360° C.—toward the lower end for sintered or recrystallized PTFE, and toward the higher end for virgin or unsintered PTFE. Some of the porous products have a fibrillar structure.

For certain embodiments, preferred fluids are liquids at 25° C. and 1 bar. Halogenated organic liquids containing fluorine and/or chlorine and, optionally, also intra-chain ether oxygen, are most preferred.

The invention also provides a variation of the above process (Process II) wherein a porous, shrink-resistant PTFE shaped article is prepared by subjecting the porous product from step (b) or step (c) to low-rate uniaxial or biaxial stretching, or wherein step (c) and stretching are performed simultaneously. Suitable fluids for use in Process II include halogenated organic fluids which may also contain intra-chain ether oxygen, and non-halogenated aromatic hydrocarbons, optionally also containing one or more substituents that are inert under process conditions. Halogen is preferably fluorine and/or chlorine.

The rate, extent, and temperature of stretching in process II of the invention are much lower, more easily controlled, less energy-intensive, and less demanding on machinery and on the PTFE itself than stretching methods of the art. Thus, the present process is an improvement over the prior art.

Moreover, the final, oriented shaped articles of this invention resist shrinkage in many wetting fluids, including those selected and exemplified in Example 67, hereinbelow. Shrink resistance is believed to result from lower orientation imposed by the relatively mild conditions of stretching in the present process compared to the prior art, and also to the unusually high degree of crystallinity of said oriented articles.

The porous, shrink-resistant PTFE shaped article prepared by process II has a mean pore size of less than about 10 µm, a porosity of at least about 40%, and a DSC melting endotherm in the range of about 315 to 333° C. with an associated heat of fusion of at least 35 J/g, and has no DSC melting endotherm at temperatures above 370° C.

Preferably, the mean pore size of the shaped article prepared by process II, is less than 2 μm, more preferably less than 1 μm. Preferred porosity is at least about 50%, more preferably at least 60%. The heat of fusion associated with the 315° C. to 333° C. melting endotherm is preferably at least 40 J/g and accounts for at least 80% of the total heat of fusion of the article.

Also included in this invention are:

(1) non-draining compositions consisting essentially of PTFE and, absorbed therein, up to about 80% by weight of a fluid penetrant;

(2) Unstretched, porous PTFE containing up to about 81% voids, preferably about 50% voids;

(3) shaped articles of (1) and (2);

(4) extruded articles such as wire, cable, fiber or tubing coated with the compositions (1) or (2), and a process for their preparation;

(5) composites comprising PTFE and up to about 50% by weight of one or more polymers, and a process for preparing said composites.

BRIEF DESCRIPTION OF THE DRAWINGS

FIG. 6a shows the film of Comparative Example 1 after exposure to isopropyl alcohol for 88 hours at room temperature.

FIG. 6b shows a film of Example 65 after exposure to isopropyl alcohol for 88 hours at room temperature.

FIG. 6c shows a film of Example 33 after exposure to isopropyl alcohol for 88 hours at room temperature.

FIG. 6d shows a film of Example 55 after exposure to isopropyl alcohol for 88 hours at room temperature.

FIG. 6e shows a cardboard disk of 2" diameter which represents the template from which samples 6a–d were prepared prior to exposure to the alcohol.

DETAILS OF THE INVENTION

Figure 1:
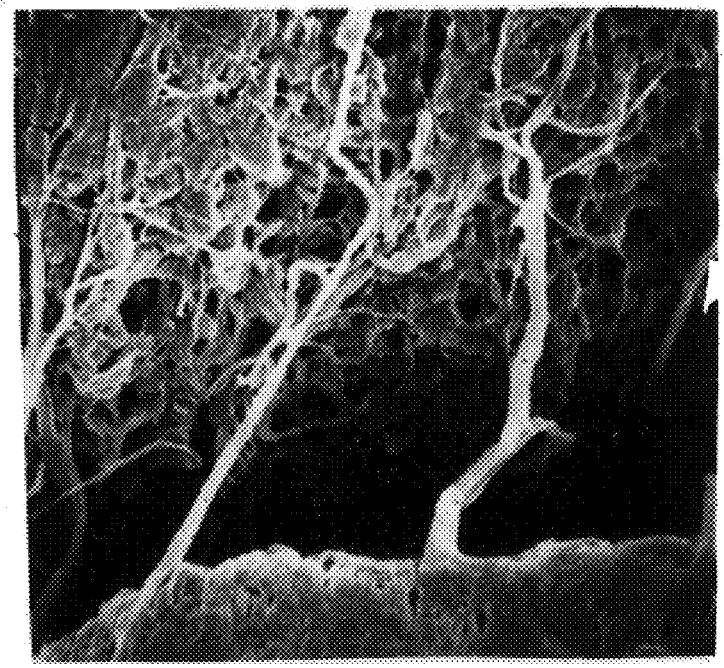
FIG. 1 is a scanning electron micrograph showing the interior of a sample comprising a mass of interconnecting fibers as produced by Example 1.

In the process (I) of the present invention for introducing porosity into PTFE, as-polymerized PTFE and melt-recrystallized PTFE are equally suitable starting materials. These may be in the form of particles or shaped articles such as film, sheet, fiber, rod or billet. The PTFE is contacted with an excess of a fluid which penetrates and swells but does not dissolve or eliminate viscoelastic memory from the PTFE under process conditions, and heated therein at a temperature in the range of about 250–400° C.

By "excess fluid" is meant substantially more fluid than is required to penetrate and swell the polymer fully under process conditions; i.e., substantially more than about 80% of the volume occupied by the unswollen polymer.

When the fluid is a relatively volatile liquid, vapor or gas, the process may be operated under pressure. Operating pressure for the invention process is from about atmospheric pressure to about 300 MPa or higher. The starting PTFE may be immersed in unheated fluid and then heated to the operating temperature, or immersed in fluid previously heated to the operating temperature. It is preferable, but not essential, to completely envelope the PTFE in fluid. The polymer should preferably remain completely enveloped by the fluid throughout the fluid contacting procedure. Precautions should be taken to insure that fluids causing adverse chemical reactions under process conditions are avoided.

In the invention process (II) for preparing stretched, porous, shrink-resistant PTFE shaped articles, conventionally formed shaped articles, such as film, fiber or billet, of PTFE, are contacted with an excess of an appropriate organic fluid in which the PTFE is insoluble or of limited solubility under process conditions, and heated therein at a temperature at or near the melting point of the PTFE under said process conditions. The starting article may be immersed in unheated fluid and then heated to the operating temperature, or immersed in fluid previously heated to the operating temperature. The polymer should preferably remain completely enveloped by the fluid throughout the fluid contacting procedure.

As indicated above, the appropriate temperature in the invention process should be sufficiently high to permit high fluid uptake but must not exceed that required to maintain the shape of the starting PTFE article under process conditions. Suitable process temperatures are at or near the melting point of the PTFE under process conditions. Factors affecting the appropriate temperature include the swelling power of the selected fluid, the crystalline morphology of the PTFE, the duration of exposure in step (a), and the surface/volume ratio of the PTFE article. Temperatures in the range of 290–360° C. are usually suitable.

Preferred fluids for use in processes I and II include halogenated organic liquids containing fluorine and/or chlorine and, optionally, also ether oxygen. Non-limiting examples of such liquids include chlorobenzene, fluorobenzene, 1,2-dichlorobenzene, benzotrifluoride, perfluorodimethylcyclobutane, perchloroethylene, Freon®-113 (1,1,2-trichloro-1,2,2-trifluorethane), Freon®-114 (1,2-dichloro-1,1,2,2-tetrafluoroethane, 1,1-difluoro-1,2,2,2-tetrachloroethane, 1,2-difluoro-1,1,2,2-tetrachloroethane, perfluoro-n-butyltetrahydrofuran, Krytox® perfluorinated oils (perfluoropropene oxide oligomers), pentafluoroethane, chloroform, methylene chloride, 1,1,2-trichloroethylene, carbon tetrachloride, and mixtures thereof. Higher boiling perfluorinated alkanes and perfluorinated cycloalkanes, such as perfluorotetradecahydrophenanthrene, which are strong solvents for PTFE, may be suitable when mixed with one or more fluids which reduce the solvent power of said alkanes or cycloalkanes or, alternatively, the PTFE can be contacted with said alkanes or cycloalkanes for a sufficiently short duration and/or at a sufficiently low temperature that the PTFE is not significantly dissolved and suffers no significant loss of shape. The perfluorinated alkanes and cycloalkanes can be made by fluorination of the corresponding hydrocarbon compound, see, for example, British Patent 1,281,822.

By "dimer" herein is meant a byproduct from the fluorination of phenanthrene using a combination of CoF3 and fluorine, as described in British Patent 1,281,822. When phenanthrene is thus fluorinated to perfluorotetradecahydrophenanthrene, a higher boiling fraction is obtained upon fractional distillation of the crude liquid product. This fraction has a boiling point in the range of 280° C. to about 400° C. at atmospheric pressure, typically about 316–340° C. It has a small amount of olefin and a very small amount of hydrogen in it which can be further reduced by post-fluorination. It is believed that most of this mixture consists of the general structure

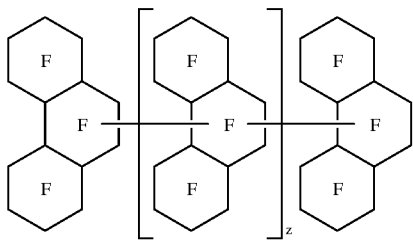

wherein z is 0, 1 or 2. Also believed to be present in smaller quantities are compounds from ring fusion and/or ring opening of the above compounds or their precursors such as

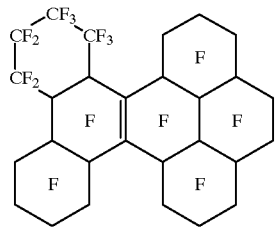

from the compound where z is 0 (it is not possible to say with assurance that this particular isomer is in the mixture— it is merely illustrative of one possible structure consistent with the analytical data and the synthetic method). Similar fused structures from the compounds where z is 1 or 2 are also believed to be present. Although traces of hydrogen are present, the location has not been determined.

Other fluids suitable for processes I and II include non-halogenated aromatic organic liquids such as, for example, toluene, benzene, anisole, and mixtures thereof with halogenated fluids. Other non-halogenated fluids suitable for process I include cyclohexane, diethyl ether, ethyl acetate, $C_{1-4}$ alcohols, tetraethoxysilane, water, and mixtures thereof with halogenated fluids. Inorganic liquids such as the tetrachlorides of titanium, silicon and tin, and the trichlorides of iron and bismuth are also suitable fluids for process I, as are gases such as ammonia, nitrogen, and sulfur dioxide. Fluid swelling power can be increased by operating the process at elevated pressure.

In the present processes, heating and pressure are maintained for a period of time dependent on the temperature, pressure, solvent power and volatility of the penetrating fluid being used, and on the dimensions of the sample. The required time may extend from less than 1 minute to several hours, generally decreasing as the swelling power of the penetrating fluid increases. As previously noted, the contact time between PTFE and fluid penetrant under processing conditions should be sufficiently short to avoid significant dissolution of the polymer, or loss of viscoelastic memory therein. "Viscoelastic memory" is herein defined as the ability of the PTFE starting material to retain or regain its original shape, although its original dimensions may increase under the conditions of the invention process.

One skilled in the art will understand that a "shaped article" is one that essentially has its own shape without external confinement or support.

It is important in the practice of the invention that viscoelastic memory and hence the shape of the PTFE starting material be retained throughout the process. For example, if the polymer is introduced in the form of film or rod, film or rod are recovered at the end of the procedure without significant change in shape, although the dimensions of said shape may increase. It should be understood that PTFE is not removed, e.g., by extraction, during the invention process; as demonstrated in the Examples, no loss in weight of polymer is detected. The polymer content of the initial (unextracted) products of the present process is greater than about 20% by weight. These products are not free-draining. Higher boiling fluids retained by these products may not be removed easily, e.g., by pressing or evaporation, and may require hot extraction with a solvent such as Freon®-113. Removal of high boiling liquids is particularly difficult and, for this reason, use of thinner sections of PTFE and more volatile fluids is preferred.

In process II, if the solvent-treated, unstretched, porous intermediate article is not in a form suitable for stretching, it may be converted to such a form by conventional procedures, such as, for example, skiving. Forms suitable for stretching include, but are not limited to, fibers, hollow fibers, film and sheet.

By "porous" products is meant products having a significant void content which are permeable to gases. The terms "void content," "porosity," and "% voids" are herein used synonymously. The method of calculation of % voids used herein is to determine the difference in density between the starting resin and that of the porous product made therefrom in the practice of this invention, and divide said difference by said starting resin density. The result multiplied by 100 is the % voids. Density of the starting resin is determined preferably by a direct volumetric technique such as helium pycnometry, but any generally accepted technique may be employed. Density of the porous product of this invention was determined by measuring the weight of a specimen of known dimensions. The unstretched porous products of processes I and II have void contents (porosity) of up to at least about 81%. Both open and closed voids are thought to be present. Preferred void content of the unstretched porous articles of process II is about 15 to 35%. Stretching of the latter articles in process II increases porosity up to 50% and higher. The porous products of process I of the invention may be fibrillar (FIGS. 1–3), have a relatively high surface area, and are semi-crystalline with a heat of fusion of at least 35 J/g. The products are particularly useful as insulation, as gas permeable articles including membranes and diaphragms, and as catalyst supports and filters. As demonstrated in the Examples, porosity of the products is shown by the reduced density of the PTFE products measured on dry, essentially liquid-free samples, by increased surface area, and/or by measurement of gas transmission through membranes of the product.

A major advantage of the present process is the ability to introduce porosity into shaped articles of PTFE without loss of shape. Thus, film, fiber, wire and cable coatings, tubing and the like can be rendered porous without the necessity to refabricate the article. As retention time under processing conditions can be quite short, the process is suitable for continuous operation. For example, PTFE film or fiber, or PTFE coatings on wire or cable, can be rendered porous in a continuous operation wherein the article is drawn through a bath containing an appropriate fluid penetrant (Example 31) heated to an operating temperature of at least about 250° C. The latter method is particular suitable in process II for preparing porous film or fiber for subsequent uniaxial or biaxial stretching to form the final invention products. Alternatively, a billet of PTFE fabricated by compaction of virgin PTFE powder may be subjected to fluid penetration in a sealed pressure vessel. After optional fluid removal, the billet is skived into film and stretched to form the final product. As indicated, porosity of the intermediate invention products is substantially further improved by subjecting said products to uniaxial or biaxial stretching.

The porous PTFE products of process I of this invention can be used to prepare composites of PTFE with one or more additional polymers, wherein said additional polymers occupy pores or voids in a matrix structure formed by the porous PTFE. The composites may be prepared by infusing one or more liquid and/or gaseous monomers, under pressure if necessary, together with appropriate polymerization initiators, into the porous PTFE previously prepared according to the invention process. Suitable monomers include, but are not limited to, ethylene, halogenated ethylenes, methacrylate and acrylate esters such as methyl, ethyl and butyl methacrylates and methyl, ethyl and butyl acrylates, styrenes, urethanes, polymerizable epoxides, difunctional monomers such as dimethacrylates and diacrylates and diglycidyl methacrylate to induce crosslinking, and the like. The selection of appropriate polymerization initiators will depend on the monomers chosen and will be apparent to those skilled in the art of polymerization. For example, a,a'-azobisisobutyronitrile (VAZ0-64®) is a well known free radical polymerization catalyst suitable for the polymerization of monomers such as methacrylates, acrylates, di(meth) acrylates, styrenes and the like.

The monomers may be polymerized in situ by the application of heat and/or irradiation such as UV or electrons. The PTFE composites prepared as described exhibit low friction similar to PTFE itself but have generally higher modulus and creep resistance. The composites are useful in load bearing applications including gaskets and seals.

A separate utility for the non-draining PTFE/absorbate composition of the invention is as an improved lubricating surface, e.g., for brake cable. When the PTFE/absorbate composite is flexed, a small amount of the absorbate exudes to the surface at the flex point; it is promptly reabsorbed when the stress is removed.

Any type of fully polymerized, high molecular weight, crystalline or partly crystalline PTFE is operable in the invention processes. The PTFE may be in any form; for example granular, fine powder, or fabricated into shaped articles. By "fine powder" is meant a coagulated and dried PTFE product of emulsion or dispersion polymerization. By "granular" is meant a product of suspension polymerization which may optionally be milled. By "PTFE" is meant polytetrafluoroethylene homopolymer and copolymers of polytetrafluoroethylene, which may contain minor amounts of repeat units of other monomers, providing said copolymers are of high molecular weight, crystalline, and non melt-fabricable, and their viscoelastic memories are not significantly diminished by the penetrating fluids under process conditions.

The PTFE polymer suitable for the practice of this invention is characterized by a melting point in the range of 315 to 333° C., preferably about 327° C., and a heat of fusion of less than about 35 J/g, preferably 25–30 J/g, which melting point and heat of fusion is determined by Differential Scanning Calorimetry (DSC; ASTM D3418-82, D4591-87) from a specimen which has, prior to said determination of melting point and heat of fusion, been heated in the DSC at least 20° C. above its melting point and recrystallized from the melt at a cooling rate of 1° C./min from 20° C. above its melting point to about 250° C. or lower. The PTFE resin preferred for the practice of this invention, as hereinabove defined, is known in the art to be of a molecular weight of about 10–30 million. "Melting point" refers to the temperature at the peak of the DSC melting endotherm.

By "crystalline PTFE" is meant PTFE having a heat of fusion of about 65 J/g in the virgin, as-polymerized state.

DSC is also employed for characterizing the porous products of this invention in their as-fabricated state. For this purpose, the as-fabricated sample is subject to a single heating at 10° C./min from ca. 100° C. to ca. 380° C., the number of endotherms being determined and the melting points and heats of fusion associated with each endotherm determined. (ASTM D3418-82, Paragraphs 10.1.1 and 10.1.2).

The actual heat of fusion and crystallinity of a given starting PTFE will depend on its fabrication history. The starting PTFE employed in the invention process, again depending on its fabrication history, has at least one crystalline melting point in the temperature range of about 315° to about 350° C. However, the unstretched porous products of process I of the invention have one crystalline melting point, said melting point lying in the range of about 315 to 333° C.

It has been discovered that pore size in the porous products of process II of the invention can be controlled by controlling the fluid used, fluid pressure and rate of cooling of the liquid-treated porous PTFE precursor articles. Such cooling-step control also affects the degree of crystallinity in said articles. Fluid-treated porous PTFE articles (porous precursors) of process II that are suitable for conversion by stretching into the final porous products of the invention are characterized by a melting point of ca. 325–330° C. and an associated heat of fusion in the range of 35–65 J/g, which heat of fusion represents at least 80%, and usually 100%, of the total heat of fusion of the specimen.

It is known in the art that conventional fabrication of the PTFE resin suitable for the practice of this invention results in fabricated articles exhibiting a melting point of ca. 325–330° C. and an associated heat of fusion in the range of 25–30 J/g. It is further known in the art that degradation of PTFE during processing can result in a higher heat of fusion associated with lower molecular weight polymers produced by that degradation. However, in that case, the higher heat of fusion is retained upon a second heating following recrystallization at 10° C./min or more slowly after the first heating in the DSC, as described hereinabove.

In the case of the porous articles of this invention, the higher than expected heat of fusion is observed only upon the first heating in the DSC. Following melt-recrystallization and reheating, the heat of fusion is found to be ca. 30 J/g, as is expected for the undegraded resin suitable for the practice of this invention. Thus, the unexpectedly high heat of fusion of the porous articles of this invention is inherent in those products and not a result of molecular weight degradation during processing.

It has been found in the practice of the invention process that porous precursors of lower crystallinity, as indicated by a heat of fusion toward the lower end of the above range, are more difficult to stretch. Small defects appear to be more detrimental to the integrity of a less crystalline precursor during stretching, particularly when stretching more than fourfold on an areal basis. However, precursor film of lower crystallinity made from fine powder PTFE of higher molecular weight proved more likely to stretch without breaking than that made from granular PTFE. For this reason, the finest pore size films were made from the fine powder PTFE.

In one embodiment of process II wherein unstretched, porous precursors are prepared and then converted into the final stretched, porous products of the invention, virgin PTFE resin in a mold is first cold compacted into a billet or cylindrical preform by placing the mold between the platens of a hydraulic press and applying pressure. The powder compaction step may be carried out below or above room temperature with appropriate adjustments made in pressure and dwell time (time held at pressure) to ensure that the resulting billet has sufficient integrity for further handling. At room temperature (about 20 to 35° C.), pressures of about 2000 to 5000 psi (14 to 35 MPa) were suitable, with dwell times of about 1 to 120 minutes. Suitable billets can be formed from either granular or fine powder PTFE resins; the former normally require lower pressure and shorter dwell time. Billets so formed should have a specific gravity of at least about 1.7, preferably at least 1.9. The billet so formed may be conventionally sintered before further handling, but such sintering is unnecessary in the practice of this invention.

The billet is placed in a pressure vessel and immersed in an appropriate fluid and heated to a temperature close to the melting point of the polymer in the presence of the fluid under process conditions, and held for a time sufficient for the fluid to uniformly penetrate the billet, but not change the shape of the billet, as discussed above. Temperatures in the range of about 320 to 360° C. are suitable for many fluids.

Following the hold period at the selected processing temperature, the billet is subjected to slow, controlled cooling to about 50 to 100° C. below the processing temperature. The hold period and cooling rate will depend upon the solvent power of the fluid, process temperature and pressure, and billet thickness.

Following treatment in the pressure vessel, the billet so processed is freed from unabsorbed fluid. Absorbed fluid may optionally be removed at any convenient point in the process, by any convenient means such as, for example, extraction, evaporation or suction.

The billet may be skived into continuous film or sheet of any desired thickness, by conventional methods. The skived film or sheet is then stretched either biaxially or uniaxially about 300–1000% on an areal basis at rates of about 1% to 1,000%/second, preferably about 10% to 1,000%/second, most preferably about 100% to 500%/second, at temperatures in the range of about 20 to 150° C., preferably 80° to 120° C. Stretching at higher rates within the specified range results in somewhat finer pores.

Stretching may be accomplished by any convenient means including batchwise using, e.g., a pantograph, or continuously using a machine direction stretcher and a tenter frame in tandem, or using a continuous biaxial orientation machine.

The porous, shrink-resistant PTFE shaped articles of this invention exhibit a mean pore size of less than about 10 $\mu$m, a porosity of about 40% or higher, a melting transition with a peak in the range of 315 to 333° C. with an associated heat of fusion of at least 35 J/g and no endotherm above 370° C. The shaped articles of the invention exhibit a morphology comprising interconnecting nodes and fibrils, said nodes being smaller or equal in size to said fibrils.

The porous, shrink-resistant PTFE shaped articles have outstanding chemical inertness and resist undesirable physical changes over a wide temperature range. The porous articles can be provided in many shapes such as, for example, film, sheet, filaments, tubing, rings and rod, and are useful in a wide variety of applications, including, but not limited to: filtration media for separating solids from fluids (gases and liquids); semi-permeable membranes for separating gases or gases and liquids; thermal and electrical insulation; protective clothing (for example, space suits, cleanroom suits, waterproof rainwear, gloves, footwear, socks, undergarments, medical drapings and garments,); sports equipment (for example, tents, sleeping bags); medical materials (for example, vascular, ligament or tendon prostheses, suture needle holders, damming materials, dental floss); seam and sealing tape; gaskets and other load-bearing articles.

In many of the applications where the articles of this invention find utility, advantage is taken of the pore structure which allows the selective transmission of fluids through the article, permitting many types of filtration or separations. An example is transmission of air and water vapor, but not liquid water, through articles of the invention.

It is often advantageous to bond or laminate the invention articles to other materials for, e.g., greater support, comfort or durability; bonding agents are able to significantly penetrate the pore network and, after curing, become locked therein. Certain perfluorinated alkanes and cycloalkanes such as perfluoro(tetradecahydrophenanthrene) and "dimer" described hereinabove, having high solvent power for PTFE, can effectively bond or laminate the invention articles without significantly penetrating the pore network. Any adhesive capable of bonding directly to PTFE will be suitable for forming laminates of the invention articles.

Methods of using the present porous, shrink-resistant PTFE shaped articles, including laminated materials, electrical and thermal insulation, protective materials, bearing materials, film, tubes, filaments, rods and the like are essentially those already described by Gore and Associates and in related art for porous PTFE articles prepared by different processes. Such methods, including laminations and bonding, are described in U.S. Pat. Nos. 5,095,779, 5,128,209, 5,086,914, 4,187,390, 4,194,041, 4,978,813 and 4,208,745 herein incorporated by reference; and in numerous other U.S. Patents assigned to W. L. Gore & Associates, Inc. or related entities.

The invention is further illustrated with reference to the following examples: Examples 1–31 relate to the introduction of porosity into PTFE articles by treatment with fluid penetrants at elevated temperatures. Example 32 relates to the use of a porous product to prepare a polymer composite. Temperatures are expressed in degrees Celsius and percentages are by weight unless otherwise indicated.

EXAMPLE 1

Preparation of Porous Polytetrafluoroethylene by Treatment with Krytox® Vapor

A piece of consolidated polytetrafluoroethylene (PTFE) was suspended in refluxing Krytox®-143AZ fluorinated (perfluoroalkylpolyether) oil vapors at 330 to 335° C. for 2 h. The system was protected by a nitrogen atmosphere. The physical changes noted in the sample were as follows:

|  | Before | After | Change, % |
| --- | --- | --- | --- |
| Thickness, cm | 1.35 | 1.75 | +30 |
| Length, cm | 4.45 | 4.50 | +1 |
| Width, cm | 2.65 | 2.48 | −6 |
| Weight, g | 37.32 | 41.28 | 10.6 |

The product contained 3.96 g or 9.6 weight % Krytox® and was more slippery than the initial PTFE sample. About 3.1 of the Krytox® was pressed out when the product was pressed between paper sheets under 15,000 psi pressure.

The above experiment was repeated except that the heat treatment was extended to 28 h. The product was found to contain 23.5 weight % Krytox®. A 2.47 g piece of the sample was extracted for about 24 h with Freon®-113 (F-113, 1,1,2-trichloro-1,2,2-trifluoroethane) and dried to constant weight. The sample piece now weighed 1.872 g, indicating a weight loss of 0.60 g or 24.3%. A scanning electron micrograph showed that the interior of the sample was comprised of a mass of interconnecting fibers (FIG. 1).

The above experiment was repeated except that the heat treatment was continued for 18 h. The product contained 17.6 wt % Krytox® and had the following physical properties compared with the PTFE starting material:

| Physical Properties of PTFE/Krytox ® Composites | | |
|---|---|---|
| | Starting PTFE | PTFE/Krytox ® Composites |
| Tensile Properties | | |
| Tensile Str, psi | | |
| Yield | 2046 | 574 |
| Max | 3672 | 2915 |
| Break | 3671 | 2550 |
| Elongation, % | | |
| Yield | 86.7 | 213 |
| Break | 230 | 370 |
| Modulus, Kpsi | 89.5 | 22.5 |
| Izod Impact | | |
| ft lb/in of notch | 1.87 | 1.36 |
| Deformation, % | | |
| (23°, 24 h, 800 psi) | 2.5 | 9.8 |
| Surface Area, m2/g | 0.0019 | 5.42* |

*Measure after removal of Krytox ® by extraction with F-113.

EXAMPLES 2–26

Preparation of Porous PTFE, Various Fluids

In Examples 2–26, sections of PTFE plaques, measuring 1.5×0.125×5 or 6 in., were placed in a 1 liter monel corrosion-resistant vessel. The plaques were fabricated by either sintering or cold pressing; in the Examples under "Prep", hot compression molded samples are coded "H", cold pressed and sintered samples are coded "S". The liquid or vapor used to prepare the porous PTFE product was poured into the vessel or, if gaseous, introduced into the cold vessel under pressure. The vessel and contents were then heated to the test temperature. After heating for a prescribed time, the vessel was cooled to room temperature and the pressure was released. The vessel was then opened and the sample was retrieved.

Figure 2:
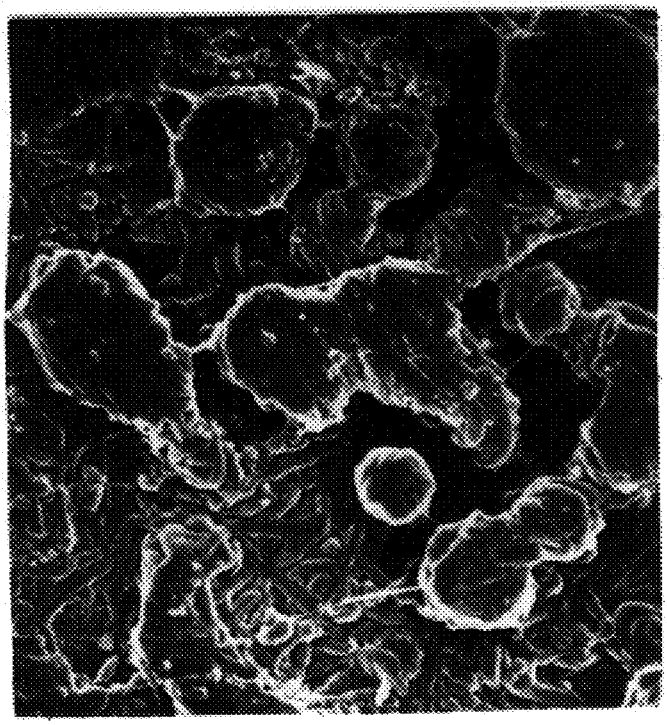
FIG. 2 is a scanning electron micrograph showing the product of Example 23.
Figure 3:
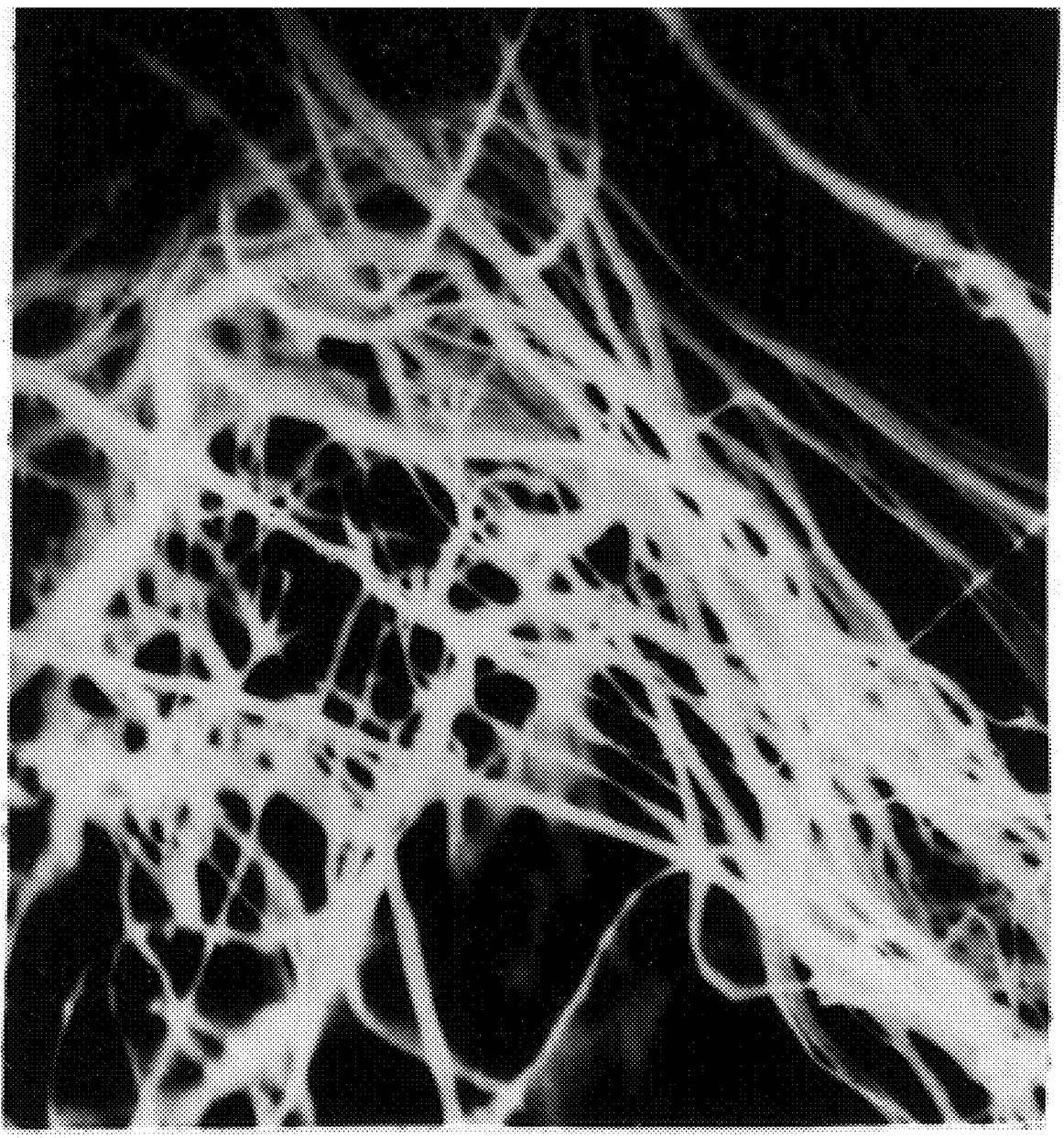
FIG. 3 is a scanning electron micrograph showing the product of Example 26.

In Examples 2 and 3, perfluorinated liquids were used to prepare porous products according to this invention. In Examples 4–10, partially fluorinated liquids, or mixtures thereof with non-fluorinated liquids, were used. In Examples 11–26, unfluorinated liquids or gases were used to prepare porous PTFE products. Examples 22–26 employed non carbon-containing compounds. The processing conditions and the densities of the fluid-free porous products obtained in Examples 2–26 are summarized in Table 1. Physical properties of products obtained in Examples shown in Table 2. Scanning electron micrographs of products of Examples 23 and 26 are shown in FIGS. 2 and 3.

TABLE 1

| | | | Conditions | | | |
|---|---|---|---|---|---|---|
| Ex. | Prep | Fluid. | Temp (° C.) | Time (h) | Pressure (psi, gage) | Density (g/mL) |
| 2 | H | HFPa cyclic dimer | 340 | 2 | 1130 | 1.80 |
| 3 | H | iso $C_6H_{14}$ | 350 | 3 | 1100 | * |
| 4 | H | FC-20a | 350 | 4 | 1100 | 1.81 |
| 5 | H | F-125a | 345 | 2 | 3800 | 1.55 |
| 6 | H | F-113 | 335 | 4 | 1310 | 1.77 |
| 7 | H | F-113 | 350 | 2 | 1450 | 1.79 |
| 8 | H | F-113 + Krytox ® | 350 | 2 | 1360 | 1.67 |
| 9 | H | $CFCl_4$ + F-113 | 350 | 1 | 1100 | 1.71 |
| 10 | H | Cyclohexane + iso$C_6F_{14}$ | 250 | 1 | 1360 | 1.73 |
| 11 | H | $CCl_4$ | 350 | 2 | 1190 | 1.46** |
| 12 | H | $CCl_4$ | 320 | 3 | 880 | 1.94 |
| 13 | H | TCEa | 300 | 3 | 395 | 1.65 |
| 14 | H | $CO_2$ | 350 | 2 | 3260 | 1.96 |
| 15 | H | Cyclohexane | 350 | 2 | 1070 | 1.72 |
| 16 | H | Methanol | 350 | 2 | 3800 | 1.67 |
| 17 | H | Methanol + Cyclohexane | 350 | 1 | 2600 | 1.86 |
| 18 | H | Ethanol | 340 | 1 | 2700 | 1.84 |
| 19 | S | $(C_2H_5)_{20}$ | 340 | 1 | 2300 | 1.91 |
| 20 | S | Et Acetate | 340 | 1 | 1800 | 1.86 |
| 21 | S | Toluene | 340 | 2 | 870 | 1.60 |
| 22 | H | $SO_2$ | 350 | 2 | 2038 | 1.95 |
| 23 | H | Water | 350 | 2 | 2300 | 2.08 |
| 24 | H | Water | 325 | 4 | 1690 | 2.15 |
| 25 | H | $NH_3$ | 340 | | 3200 | 1.86 |
| 26 | H | $N_2$ | 340 | 2 | 15,400 | 1.61 |

*Surface area, 5.4 m$^2$/g; surface area of starting PTFE, 0.084 m$^2$/g.
**Surface area, 6.0 m$^2$/g.
aHFP = Hexafluoropropene
FC-20 = Perfluoro-n-butyltetrahydrofuran
F-125 = Pentafluoroethane
TCE = Tetrachloroethylene

TABLE 2

Properties of porous PTFE after compression at 150° C. and 13,500 psi

| Property | Ex. 5 | Ex. 6 | Ex. 7 | Ex. 8 | Ex. 12 | Ex. 24 |
|---|---|---|---|---|---|---|
| DSC | | | | | | |
| M.P. ° C. | 332 | 331 | 332 | | 331 | 330 |
| Heat of Fusion | 54 | 57 | 61 | | 43 | 30 |
| Density g/ml | 2.04 | 1.99 | 1.79 | 2.04 | 2.11 | 2.17 |
| Tensile Properties | | | | | | |
| Yield Stress (psi) | 812 | 1278 | 1360 | 802 | 1291 | 1722 |
| Max. Stress (psi) | 827 | 1837 | 2209 | 1641 | 1896 | 2333 |
| Breaking Stress (psi) | 293 | 1816 | 2207 | 1628 | 1881 | 2316 |
| Elongation at Yield (%) | 5.0 | 14.4 | 5.0 | 13.3 | 11.7 | 43.0 |
| Elongation at Break (%) | 30.5 | 247 | 358 | 146 | 255 | 205 |
| Tensile Modulus (kpsi) | 125 | 140 | 158 | 92.2 | 131 | 178 |
| Izod Impact (ft-lb/in notch) | 1.7 | 2.3 | 2.4 | 2.0 | 2.0 | 2.6 |

EXAMPLE 27

Evidence of Porosity in a Product of the Invention

The 1 liter vessel used in the previous examples was charged with two 31 mil (0.79 mm) thick strips of sintered PTFE separated by monel plates to prevent sticking and loss of shape were immersed in $CCl_4$ and subjected to the following heating schedule:
310° C. for 30 min.
330° C. for 30 min.

340° C. for 1 h.

310° C. for 1 h.

After drying the resulting porous sheets were 38 mils thick and were porous to nitrogen gas; flow rates of nitrogen flowing through the sheets at different nitrogen pressures were:

| $N_2$ Pressure (psi) | $N_2$ Flow (mL/h) |
| --- | --- |
| 6.8 | 226 |
| 6.8 (1 h later) | 227 |
| 2.1 | 45 |
| 1.2 | 19.5 |

Similar qualitative nitrogen permeation tests were run on strips 66–164 mils (1.7–4.2 mm) thick of the porous products from Examples 2, 4–6, 9, 11, 13–16, 19–22, except that the tests were run at room temperature (21° C.) and at 6 psi nitrogen pressure. All the strips except that of Example 20 (4.1 mm) were permeable; the strip from the product of Example 20 was permeable at higher nitrogen pressures.

EXAMPLE 28

Preparation of Porous PTFE Films

PTFE films, 3 mils thick and 5 mm wide were slowly passed through refluxing Krytox®. The films were easily drawn while hot to about 5-times their original length, and, while still hot, recovered their original length when tension was released. However, if the 5-fold extension was maintained while the polymer cooled and crystallized, the films did not shrink and measured 1.5 mil in thickness. A portion of one film weighing 0.6602 g was extracted for 1 day with FC-113 and then dried to constant weight. Its final weight was 0.4153 g, indicating that the sample before extraction contained 37 weight % Krytox®. The starting film, before processing, could only be drawn 2-fold and was slightly elastomeric. The porous processed film was not elastomeric.

The rate of Krytox® adsorption by 3 mil PTFE film was measured by soaking film in hot Krytox® 143AZ for various times and measuring the amount (%) of Krytox® in the film:

| Soak Time (sec) | Krytox ® Temp. (° C.) | Krytox ® in Film (%) |
| --- | --- | --- |
| 10 | 345 | 6 |
| 30 | 345 | 16 |
| 60 | 345 | 16 |
| 1800 | 344 | 16 |
| 300 | 300 | 10 |
| 300 | 310 | 15 |

A 7 in×12 in.'1 in. wide externally heated monel trough containing refluxing Krytox® was used to process larger sheets of PTFE film in continuous mode. Three mil film pulled through the refluxing Krytox® at a rate of 1 ft/min was found to contain 9.3 weight % Krytox®. After removal of the Krytox® from the film by extraction with F-113 and drying, the porous film was opaque relative to the unprocessed film. The porous film lost most of its opaqueness and developed a blue hazy structure when stretched; the unprocessed film became more opaque on stretching.

Films prepared as above were extracted with F-113 and cut into 4.5 mm wide strips labelled A–E which were drawn over hot pins. Krytox® content before extraction and draw conditions are shown relative to unprocessed control film in Table 3; physical properties are shown in Table 4.

TABLE 3

| Sample | Initial Krytox ® Content, % | Draw Ratio | Draw Temp. ° C. |
| --- | --- | --- | --- |
| A | 0 | 4.8 | 345 |
| B | 0 | 4.8 | 300 |
| C | 13.5 | 3.2 | 300 |
| D | 13.5 | 3.3 | 345 |
| E | 11.1 | 3.3 | 316 |

TABLE 4

| Sample | Init. Mod, gpd | Tenacity, max, gpd | Elong., % | Toughness gpd |
| --- | --- | --- | --- | --- |
| A | 4.74 | 0.70 | 27.6 | 0.0991 |
| B | 3.91 | 0.65 | 33.1 | 0.1105 |
| C | 2.68 | 0.643 | 64.2 | 0.2117 |
| D | 2.62 | 0.717 | 69.4 | 0.2524 |
| E | 2.95 | 0.617 | 67.5 | 0.2229 |

It was found possible to draw the films processed with Krytox® in two directions.

EXAMPLE 29

Preparation of Large Sections of Porous PTFE

In the following experiment, a 1 gallon Hasteloy autoclave was charged with Teflon® TFE resin grade 7A, from DuPont, in the form of a sintered rod weighing 1248.4 g and measuring 5.75 in.×3 in. diameter with a 0.94 in. core hole through the length. F-113 was added to the autoclave such that the PTFE rod, standing on end, was completely immersed in about 7 in. of the liquid. The autoclave was closed and heated according to the following schedule:

To 200° C. and held for 30 min;

250° for 30 min;

300° for 30 min;

350° for 4 h;

330° for 1 h;

310° for 2 h;

cool to ambient temperature.

The product weighed 1527 g, indicating a weight gain of 279 g, and measured 6.6 in. long×3.1 in. diameter. The core diameter was 0.98 in. After drying to remove the F-113 the rod weighed 1248.5 g and had a density of 1.81 g/ml. Film skived from the rod could be both uniaxially and biaxially stretched.

The above experiment was repeated with similar billets of Teflon® 7A which had been either sintered or cold pressed, wherein the F-113 was replaced, respectively, with methanol, water, CCl4, Krytox®-143 AZ and cyclohexane.

EXAMPLE 30

Porous Products from PTFE Powder

Teflon® 7C virgin TFE Granular Resin molding powder (94.3 g) was immersed in refluxing Krytox® for 20 h. On cooling, the recovered product was in the form of a soft lump weighing 178 g and containing 47% Krytox®. The lump reverted to powder when gently agitated. Films and other shaped objects could be prepared by hot pressing.

EXAMPLE 31

A mixture of oligomers ("dimer"), which is a by-product of the fluorination of phenanthrene was decolorized by passage over a hot bed of basic alumina (ICN Biochemicals); this mixture is an embodiment of "dimer", as described above. Distillation of the mixture under reduced pressure provided 7 fractions, the lightest of which boiled at 117° C. at 0.6 mm (80 Pa), and the heaviest boiled at 255–287° C. at 0.2 mm (27 Pa). The fractions were not further characterized.

A test tube 30 cm long of 3.4 cm diameter was half filled with the "dimer" mixture and placed in a Woods' metal bath at 340–360° C. The "dimer" refluxed gently at 316–318° C. Silvered copper wire coated with PTFE was plunged into the hot liquid and then into F-113 to cool and extract the "dimer".

TABLE 5

| Sample | Coated Wire, mil | Initial Coat, mils | Time, sec. | Final Coat, mils | Coating Dens.g/mL |
|--------|------------------|---------------------|------------|------------------|-------------------|
| A | 43 | 18 | 20 | 22.5 | 1.6 |
| B | 30 | 2.5 | 60 | 4.0 | 1.3 |
| C | 30 | 2.5 | 30 | 4.0 | 1.3 |

A = Silver coated Cu, multistrand, coated with sintered PTFE
B,C = Silver coated Cu, multistrand, coated with unsintered PTFE In similar experiments, where the "dimer" was employed as-received without decolorization, substantially the same results were observed.

EXAMPLE 32

A sheet of PTFE having continuous pores, prepared by treatment in refluxing Krytox®, as described in Example 28, was immersed in liquid methyl methacrylate (MMA) containing 0.2% by weight of VAZO-64® polymerization initiator and centrifuged for about two hours, during which time MMA/initiator was absorbed by the PTFE until no further weight gain was observed. The "composite", together with a small amount of additional MMA/initiator, was then placed between glass plates and the "sandwich" was heated at 60° C. for 4 hours, then at 80° C. for 5 hours to complete the polymerization of the absorbed MMA. The resulting PTFE/Poly(methyl methacrylate) composite contained 22% by volume of poly(methyl methacrylate) and had the following physical properties, compared with unprocessed commercial PTFE sheet:

| Tensile Properties | Commercial PTFE Sheet | PTFE/PMMA Composite |
|--------------------|----------------------|---------------------|
| Tensile Strength, psi | | |
| At Yield | 2046 | 1760 |
| At Max | 3672 | 1900 |
| At Break | 3671 | 1250 |
| Elongation, % | | |
| At Yield | 86.7 | 6.7 |
| At Break | 230 | 105 |
| Tensile Modulus, kpsi | 89.5 | 168 |
| Izod Impact, ft-lb/in of notch | 1.9 | 1.05 |

Compressive creep resistance of the composite was tested as follows: A plaque of the composite 0.125 in. thick was cut into 0.5 in. squares. Four of the squares were stacked to give a 0.5 in. high cube. A similar layered cube was prepared from commercial PTFE. A pressure of 1 kpsi was applied to both cubes for 24 h at room temperature and the loss in height was measured continuously. After 24 h the cube of commercial PTFE had compressed 3.36% while the cube of composite had compressed 1.59%. Five minutes after release of pressure the % compression was 2.78 and 1.06%, respectively.

The following Examples 33–68 and Comparative Examples 1–5 relate to preparation of porous PTFE precursor articles and their conversion by stretching into the final stretched porous products of the invention.

Unless otherwise indicated, films were formed by skiving billets which had been rendered porous by elevated temperature liquid treatment in a 1 gallon Hastelloy pressure vessel. Billets were formed at room temperature by compacting 1250 g of virgin PTFE resin powder into a cylindrical preform about 15 cm high and 7.7 cm in diameter containing a concentric hole 2.4 cm in diameter. The granular resin employed was Teflon® Type 7A, the fine powder resin was Teflon® TE 3641 resin, both available from DuPont. The granular resin was formed into billets at a pressure of 2200 psi applied for 4 minutes; the fine powder, at a pressure of 4700 psi applied for 30 minutes or more. Billets were skived by mounting the billet on a machinist's lathe and employing a diamond-edged knife. Film so produced was stretched by loading square film specimens, 11.4 cm edge length, into a pantograph stretcher available from the T. M. Long Co., Inc., Somerville, N.J. Unless otherwise indicated: samples were preheated for 2 to 3 minutes before stretching, stretching rate was 75%/second, stretching temperature was 100° C., and samples were stretched biaxially at equal rates and to equal extents. No difference was detected between stretching in the two directions sequentially or simultaneously, and hence both methods have been employed herein without distinction.

Thermal analysis was performed using a System 2000 single cell differential scanning calorimeter available from TA Instruments, Inc. Wilmington, Del. In Examples 33–68 and Comparative Examples 1–5, the term "heat of fusion" refers to the "as-fabricated" heat of fusion as determined in the manner hereinabove described.

Air permeability and pore-size distribution were determined using a Porometer II instrument available from Coulter Electronics, Ltd., Luton, UK. The Porometer utilized a bubble point technique for determining the pressure at which the initial air flow was detected through a thoroughly wetted test specimen. The pore size distribution, including the mean pore size, was determined by measuring the air flow rate as a function of pressure above the bubble point. The pore-size distribution calculation, performed automatically by the Porometer, provides the diametric size distribution of a population of straight cylindrical pores which would exhibit the same pressure/flow rate data as the test membrane. Since the pores in microporous PTFE films are highly irregular in cross-section, the calculated pore sizes are relative rather than absolute. However, the method provides consistent results between samples g112 of comparable morphology, and is widely practiced in the art.

The Porometer II is unable to measure the size of pores smaller than about 0.05 $\mu$m. As some of the pores of films of the invention were smaller than 0.05 $\mu$m, the calculation of the mean flow pore size is believed to overemphasize the larger pore end of the distribution. Mean flow pore sizes given in the ensuing Examples may therefore be somewhat higher than the actual values.

Pressure in the pressure vessel was determined using a model IBH103 pressure transducer manufactured by Magnetek Transducer Products, Simi Valley, CA93065.

TABLE 6

| Ex. | Resin Type | Pressure in Pressure Vessel (psi) | Void Content in Skived Film (%) | Skived Film Heat of Fusion (J/g) | Areal Stretch Ratio | Stretched Film Thickness (μm) | Stretched Film Heat of Fusion (J/g) | % of Total Heat from 328° C. Transition | Void Content in Stretched Film (%) | Mean Flow Pore Size (μm) | Max. Pore Size (μm) | Normalized Air Perm. (l-μm/sq.cm-min-bar) |
|---|---|---|---|---|---|---|---|---|---|---|---|---|
| 33 | Fine Powder | 1216 | 20 | 40 | 4.00 | 48 | 38 | 100 | 48 | 0.07 | 0.08 | 8 |
| 34 | Fine Powder | 1588 | 21 | 40 | 4.00 | 46 | 39 | 100 | 47 | 0.07 | 0.09 | 8 |
| 35 | Fine Powder | 1588 | 21 | 40 | 4.00 | 46 | 47 | 100 | 46 | 0.07 | 0.08 | 8 |
| 36 | Fine Powder | 2097 | 25 | 43 | 4.00 | 44 | 46 | 100 | 49 | 0.09 | 0.11 | 12 |
| 37 | Granular | 1950 | 22 | 44 | 6.25 | 40 | 43 | 100 | 59 | 0.10 | 0.13 | 24 |
| 38 | Granular | 1950 | 22 | 44 | 4.00 | 53 | 44 | 100 | 51 | 0.07 | 0.13 | NA |
| 39 | Granular | 1950 | 22 | 44 | 3.10 | 54 | 44 | 100 | 44 | 0.07 | 0.14 | NA |
| 40 | Granular | 1950 | 22 | 44 | 6.25 | 41 | 41 | 100 | 61 | 0.10 | 0.14 | 22 |
| 41 | Fine Powder | 1481 | 18 | 45 | 4.00 | 46 | 44 | 93 | 50 | 0.07 | 0.10 | 9 |
| 42 | Granular | 1502 | 12 | 45 | 4.00 | 53 | 45 | 100 | 52 | 0.10 | 0.14 | 18 |
| 43 | Granular | 1450 | 13 | 46 | 4.00 | 54 | 44 | 100 | 51 | 0.10 | 0.14 | 18 |
| 44 | Fine Powder | 1796 | 24 | 47 | 4.00 | 46 | 45 | 100 | 55 | 0.08 | 0.11 | 12 |
| 45 | Granular | 1646 | 12 | 47 | 4.00 | 54 | 46 | 100 | 48 | 0.11 | 0.16 | 20 |
| 46 | Fine Powder | 2050 | 21 | 47 | 6.25 | 33 | 44 | 82 | 61 | 0.13 | 0.16 | 25 |
| 47 | Fine Powder | 2050 | 21 | 47 | 5.06 | 38 | 45 | 100 | 59 | 0.13 | 0.16 | 30 |
| 48 | Fine Powder | 2050 | 21 | 47 | 6.25 | 30 | 45 | 100 | 59 | 0.13 | 0.16 | 29 |
| 49 | Fine Powder | 2050 | 21 | 47 | 6.25 | 30 | 44 | 85 | 57 | 0.13 | 0.16 | 28 |
| 50 | Granular | 1889 | 18 | 48 | 9.00 | 34 | 45 | 100 | 65 | 0.14 | 0.15 | 31 |
| 51 | Granular | 1889 | 18 | 48 | 4.00 | 53 | 49 | 100 | 56 | 0.09 | 0.16 | 24 |
| 52 | Granular | 1935 | 13 | 49 | 4.00 | 55 | 49 | 100 | 60 | 0.14 | 0.21 | 37 |
| 53 | Granular | 1935 | 13 | 49 | 9.00 | 34 | 46 | 100 | 72 | 0.16 | 0.21 | 50 |
| 54 | Fine Powder | 2308 | 13 | 49 | 4.00 | 50 | 49 | 86 | 51 | 0.10 | 0.14 | 17 |
| 55 | Granular | 1800 | 14 | 51 | 9.00 | 36 | 49 | 100 | 74 | 0.19 | 0.25 | 67 |
| 56 | Fine Powder | 2350 | 26 | 53 | 4.00 | 54 | 54 | 100 | 61 | 0.18 | 0.25 | 47 |
| 57 | Granular | 2496 | 20 | 55 | 9.00 | 48 | 46 | 100 | 78 | 0.34 | 0.48 | 166 |
| 58 | Granular | 2536 | 18 | 56 | 9.00 | 44 | 46 | 100 | 77 | 0.29 | 0.39 | 139 |
| 59 | Granular | 2400 | 24 | 56 | 6.25 | 55 | 49 | 100 | 75 | 0.33 | 0.54 | 160 |

EXAMPLES 33–59

In these examples both fine powder and granular resins were employed. Billets were fabricated therefrom and exposed to an excess of trichlorotrifluoroethane at about 350° C. for four hours at the pressures shown in Table 6, after which they were cooled to 330° C. and held for one hour, then cooled further to 310° C. and held for two hours, after which electrical power to the heaters was turned off, and the vessel was allowed to cool to room temperature over a period of about 10 hours.

As shown in Table 6, the void content of films skived from the treated billets ranged from 12 to 26%, and of the stretched films, from 44 to 78%. Mean flow pore size and maximum pore size (related to the bubble point) ranged from 0.07 to 0.42 μm, and 0.08 to 0.64 μm, respectively. Air permeability, normalized for a one micron film thickness and 1 bar applied pressure, ranged from 8 to 166 (1-μm/cm²-min-bar), the higher permeability associated with the larger pore sizes, as expected from theoretical considerations of flow rates through porous substances.

The heats of fusion of the skived films ranged from 40 to 56 J/g, and of the stretched films, from 38 to 54 J/g. In the stretched films, the heat of fusion associated with the 320–333° C. DSC endotherm comprised at least 80% and usually 100% of the total heat of fusion of the microporous film. In none of Examples 33–59 was an endotherm above 370° C. detected.

Figure 4:
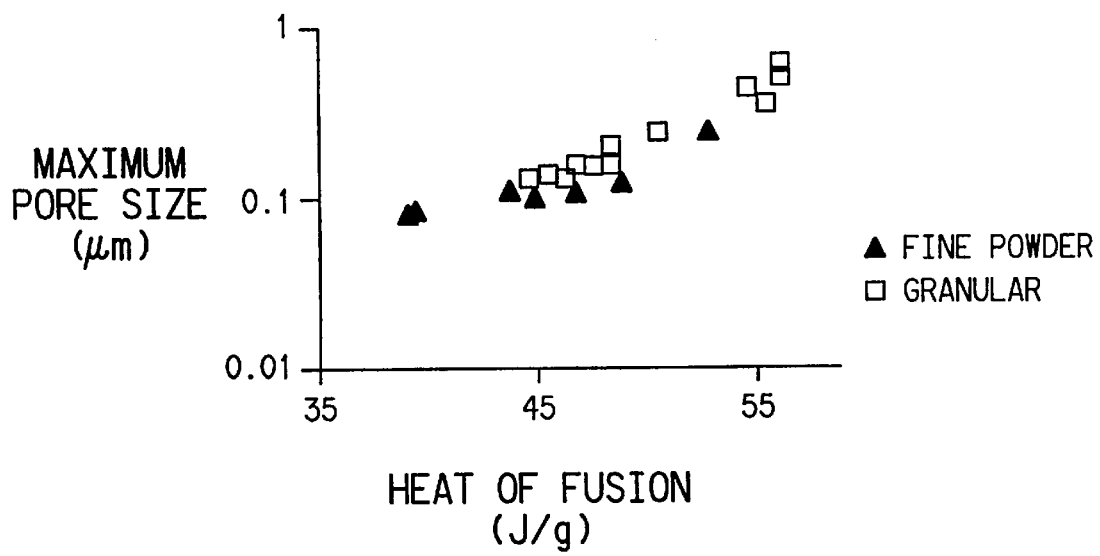
FIG. 4 is a graph of the maximum pore size of the film plotted against the heat of fusion.

These examples show that the maximum pore size in the stretched films of the invention is closely related to the heat of fusion of the associated unstretched, skived film. This is shown in FIG. 4 wherein the maximum pore size is plotted on a logarithmic scale vs. the heat of fusion on a linear scale.

Figure 5:
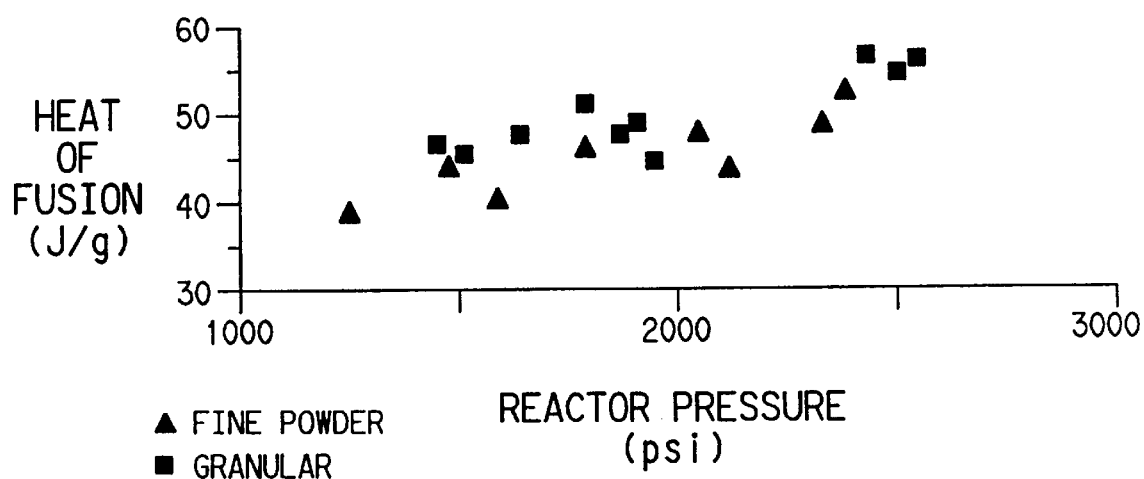
FIG. 5 is a graph of the heat of fusion of the film plotted against the reactor pressure.

A correlation is also seen between the heat of fusion of the skived film and the pressure of the fluid penetrant in the pressure vessel, as shown in FIG. 5 wherein the heat of fusion of the skived film is plotted against the maximum pressure.

COMPARATIVE EXAMPLES 1 TO 5

Four commercially available microporous PTFE films and one non-porous commercially available PTFE film were evaluated using the same methods as in Examples 33–59. Results are given in Table 7.

TABLE 7

| Comp. Ex. | Manufacturer | Film Thickness (μm) | Void Content (%) | Max. Pore Size (μm) | Mean Flow Pore Size (μm) | Air Perm. (l-μm/cm²-min-bar) | Film Heat of Fusion (J/g) | % of Total Heat from 328° C. Transition | Endotherm above 370° C. |
|---|---|---|---|---|---|---|---|---|---|
| 1 | W. L. Gore & Co. Newark DE | 83 | 78 | 0.49 | 0.30 | 204 | 39 | 33 | 1.5 J/g @ 374° C. |
| 2 | W. L. Gore & Co. Newark DE | 38 | 79 | 0.46 | 0.39 | 213 | 32 | 38 | 1.9 J/g @ 375° C. |
| 3 | Nuclepore | N.A.[a] | N.A. | 0.56 | 0.50 | N.A. | 35 | 71 | 1.4 J/g @ 374° C. |

TABLE 7-continued

| Comp. Ex. | Manufacturer | Film Thickness (μm) | Void Content (%) | Max. Pore Size (μm) | Mean Flow Pore Size (μm) | Air Perm. (l-μm/cm²-min-bar) | Film Heat of Fusion (J/g) | % of Total Heat from 328° C. Transition | Endotherm above 370° C. |
|---|---|---|---|---|---|---|---|---|---|
| 4 | Sumitomo Japan | 40 | 66 | 0.70 | 0.57 | 208 | 28 | 64 | 3.1 J/g @ 375° C. |
| 5 | DeWal Industries | 51 | 0[b] | N.A. | N.A. | N.A | 27 | 100 | None |

[a]Mounted on a Polypropylene backing.
[b]Commercially available skived PTFE film. Non-porous.

A comparison of the results in Table 7 with those in Table 6 illustrates the inventive features of the present invention. The heats of fusion of the former films were always less than 40 J/g in total, and less than 75% of that total was associated with the 320 to 333° C. DSC endotherm. All four of the films exhibited an endotherm of at least 1 J/g at a temperature above 370° C.

The thermal "signature" of the films of this invention more closely resembles that of non-porous skived PTFE film than that of the microporous films of the prior art. The principal difference in thermal signature between films of the invention and that of non-porous skived PTFE films is that the heat of fusion, and hence the crystallinity, of the former is at least about 50% higher.

EXAMPLES 60–62

These examples demonstrate that the object of this invention may be attained by stretching in one direction only, and also illustrate the effects of different rates of extension.

Films were prepared as in Examples 51 and 52, except that they were stretched 4× in the machine or longitudinal direction only. Stretch rates and results are shown in Table 8.

In Example 61, a stretching rate at the low end of the range suitable for the practice of this invention was employed, producing film well within the scope of the invention. In Example 62, a rate at the high end of the range preferred for the practice of this invention was employed, again producing film well within the scope of the present invention.

A comparison of Examples 61 and 62 shows that increasing stretch rate by about 50× (about 5000%) resulted in a pore size approximately 35% smaller and a permeability about 40% lower.

TABLE 8

Effects of uniaxial stretching and stretching at different rates on the properties of the films of this invention

| | Ex. 60 | Ex. 61 | Ex. 62 |
|---|---|---|---|
| Stretch Rate (%/s) | 75 | 7.5 | 370 |
| Thickness (μm) | 46 | 48 | 41 |
| Stretched Film Heat of Fusion (J/g) | 46 | 45 | 49 |
| Mean Pore Size (μm) | 0.10 | 0.13 | 0.09 |
| Voids (%) | 52 | 55 | 51 |
| Air Perm. (1-μm/cm2-min-bar) | 12 | 19 | 8 |
| % From 328° Endotherm | 100 | 89 | 100 |
| Endotherm above 370° C. | NONE | NONE | NONE |

These examples further show that pore size and permeability of the films of the invention are relatively independent of stretching rate over the wide range of rates suitable for the practice of the invention. This result is a clear departure from the teaching of the art, especially that of Gore and Tamaru, which is inoperable at the stretching rates employed in Examples 60–62.

EXAMPLE 63

A billet of granular PTFE was heated in the presence of an excess of 1,1 difluorotetrachloroethane for 4 hours at 335° C. and about 725 psi pressure. The billet was cooled to 300° C., held for 30 minutes, then cooled to 270° C., and held for another 30 minutes, after which the heat was shut off and the pressure vessel was permitted to cool naturally to room temperature. Film skived from the billet was stretched 4× under standard conditions to give a 26 μm thick microporous film with 56% voids, a mean pore size of 0.15 μm, and a heat of fusion associated with the 320 to 333° C. DSC endotherm of 49 J/g, which was 97% of the total heat of fusion. No endotherm was detected above 370° C.

EXAMPLE 64

A billet of granular PTFE was heated in the presence of excess carbon tetrachloride for 3 hours at 315° C. and about 1050 psi pressure. The billet was then cooled to 300° C., held for 1 hour, then cooled to 275° C., and held for another 1 hour, after which the heat was shut off, and the pressure vessel was permitted to cool naturally to room temperature.

Film skived from the billet was stretched 3.1× under standard conditions to give a 30 μm thick microporous film having 46% voids, a mean pore size of 0.10 μm, and a heat of fusion associated with the 320 to 333° C. DSC endotherm of 45 J/g, which was 100% of the total heat of fusion. No endotherm was detected above 370° C.

EXAMPLE 65

A billet of granular PTFE was heated in excess perfluorohexane for 3 hours at 400° C. and about 2950 psi pressure. The billet was cooled to 330° C., held for 1 hour, then cooled to 310° C., and held for another hour, after which the heat was shut off and the pressure vessel was permitted to cool naturally to room temperature.

Film skived from the billet was stretched 4× under standard conditions to give a 71 μm thick microporous film with 78% voids, a mean pore size of 0.18 μm, and a heat of fusion associated with the 320 to 333° C. DSC endotherm of 50 J/g, which was 97% of the total heat of fusion. No endotherm was detected above 370° C.

EXAMPLE 66

In this Example the objects of the invention are provided by a process comprising continuous film treatment. A commercially available (Furon Inc.) skived film of PTFE, about 75 μm in thickness, was fed continuously at a line speed of about 1.2 m/min via a series of rollers into a corrosion-resistant metal bath containing a mixture of oligomers ("dimer") which are a by-product of the fluorination of phenanthrene as described hereinabove, and withdrawn via a similar series of rollers to a constant speed wind-up. The bath was maintained at a temperature of about 290° C. Total residence time in the bath was about 30 seconds.

The film was extracted with trichlorotrifluoroethane to remove the absorbed fluid. The film was then stretched 9× at standard rate but at 50° C. Mean pore size was 0.09 μm, porosity was 52%, heat of fusion associated with the 320 to 333° C. DSC endotherm was 38 J/g, which was 100% of the total heat of fusion. No endotherm was detected above 370° C.

EXAMPLE 67

Disks 2" in diameter were cut from the films of Examples 33, 55, 65 and Comparative Example 1. The disks were each placed in isopropyl alcohol at room temperature for a period of 88 hours. They were then removed, laid flat, and air-dried. The film of Comparative Example 1 shriveled badly, assuming a highly irregular shape, considerable 3-dimensional bumps, and smaller in overall effective diameter. The films of Examples 33, 55 and 65 were unaffected.

Similar results were obtained in experiments as above wherein isopropyl alcohol was replaced with toluene, commercial cleaning fluid (chlorinated hydrocarbons and petroleum distillates), ethyl alcohol, Krytox® 161-40 or mineral oil.

Figure 6:
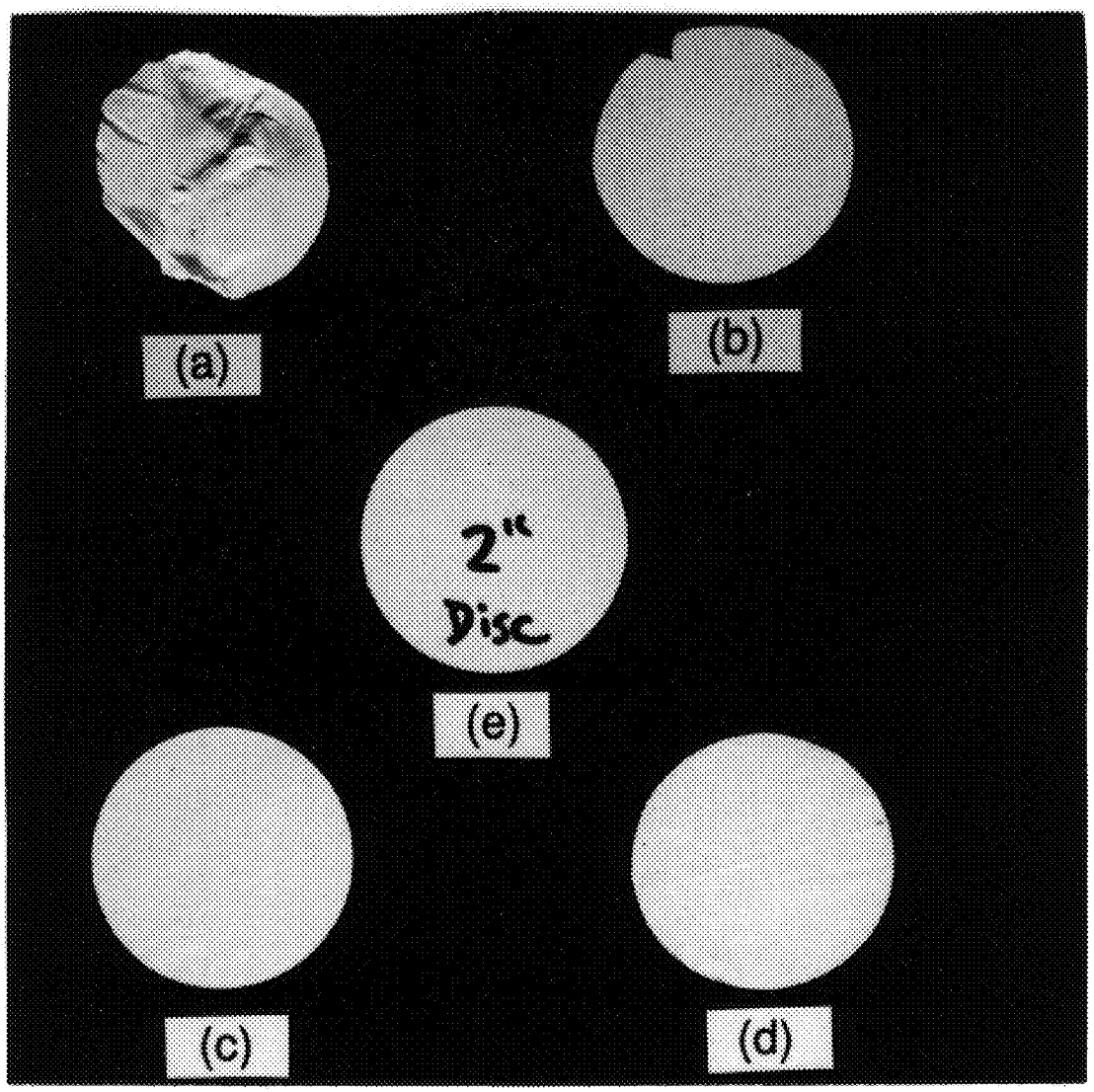
FIG. 6 (a–e) show differences in shrinkage between the files of the present invention and those of the art.

FIG. 6 (a, b, c, d and e) clearly illustrate the difference in shrinkage between the films of this invention and the prior art. In FIG. 6 (a, b, c, d and e), the 2 inch disk was a circular piece of cardboard identical in shape to each of the films prior to wetting.

The surface texture of the films of the invention were unchanged by wetting, as was the notch on the periphery of the film of Example 66.

EXAMPLE 68

A cold-pressed billet of granular PTFE, 5 15/16 inch high×3 inch diameter containing a 15/16 inch concentric longitudinal hole, weighing 1247 g, was placed in a 1 gallon hastalloy pressure vessel containing sufficient benzene so that the top of the billet was about 1 inch below the surface of the liquid. The vessel was heated to a mazimum temperature of 346° C., at a pressure of about 950 psi, and held for four hours.

The density of the billet so treated was 1.89 g/cc. The heat of fusion of the skived film was 41.4 J/g. The skived film was stretched 2x×2x at a rate of 75%/second. The resulting film was 52 μm thick, and contained 51% voids. The mean pore size was 0.10 μm. The heat of fusion of the stretched film was 41 J/g, with 100% of the heat of fusion associated with the 320 to 333° C. DSC melting endotherm. No endotherm above 370° C. was present.

EXAMPLES 69, 70 AND 71

Preparation of Porous PTFE with Hiqh Void Content

In the below Examples 69, 70 and 71, sections of commercial PTFE sheet (⅛"×3"×½") were placed in a corrosion resistant 50 mL metal vessel with the indicated mixtures of solvent. The vessel was heated to 335° C. and held at this temperature for 5 hours. The products were recovered after cooling and the weight gain was measured. The density of the liquid was also measured. This made it possible to calculate the volume fraction of liquid in the porous structure. The products all had combinations of large and small voids when the solvent was extracted out with Freon®-113.

EXAMPLE 69

The following mixture of solvents was used with the indicated weight of PTFE: 150 g Krytox®-143 AZ; 150 g Flutec®-11 perhydroperfluorophenanthrene; 19.2 g PTFE. The product was 35 g (45% by weight liquid). The liquid density was 1.93/g per mL. The liquid content was 48% by volume. The product maintained its original shape but was larger. It still retained square corners.

EXAMPLE 70

The following mixture of solvents was used with the indicated weight of PTFE: 100 g Krytox®-143 AZ; 200 g Flutec®-11 perhydroperfluorophenanthrene; 20.25 g PTFE. The product weight was 72.2 g (72% by weight liquid). The liquid density was 1.956/g per mL. The liquid content was 75% by volume. The product maintained its original shape. The product did crack because the volume increased so much the vessel could not accomodate it.

EXAMPLE 71

The following mixture of solvents was used with the indicated weight of PTFE: 110 g F-113; 300 g Flutec®-11 perhydroperfluorophenanthrene. 19.32 g PTFE. The product weight was 93.2 g (79% by weight liquid). The liquid density was 1.93/g per mL. The liquid content was 81 volume %. The product maintained its original shape but was larger; it still retained square corners. The product cracked because it had no space to expand in.

EXAMPLE 72

The following mixture of solvents was used with the indicated weight of PTFE: 100 g fluorobenzene; 200 g Flutec®-11 perhydroperfluorophenanthrene; 19.62 g PTFE. The product weighed 50.2 g (61% by weight liquid). The liquids formed two phases at room temperature so it was not possible to measure density and get volume percent.

What is claimed is:

1. A laminated structure comprising (i) a porous shrink-resistant polytetrafluoro-ethylene (PTFE) shaped article having a mean pore size of less than about 10 μm, a porosity of at least 40%, a DSC melting endotherm in the range of 315 to 333° C. with an associated heat of fusion of at least 35 J/g, and having no DSC melting endotherm at temperatures above 370° C., and (ii) a second, different shaped article bonded to (i).

2. The laminated structure according to claim 1 wherein a bonding agent bonds article (i) to second article (ii), and said bonding agent is present in the pore network of portions of article (i) that are adjacent to said second shaped article (ii).

3. A filtration medium comprising a porous, shrink-resistant polytetrafluoro-ethylene (PTFE) shaped article having a mean pore size of less than about 10 μm, a porosity of at least 40%, a DSC melting endotherm in the range of 315 to 333° C. with an associated heat of fusion of at least 35 J/g, and having no DSC melting endotherm at temperatures above 370° C.

4. A gas/liquid separatory medium comprising a porous, shrink-resistant polvtetrafluoro-ethylene (PTFE) shaped article having a mean pore size of less than about 10 μm, a porosity of at least 40%, a DSC melting endotherm in the range of 315 to 333° C., with an associated heat of fusion of at least 35 J/g, and having no DSC melting endotherm at temperatures above 370° C.

5. The separatory medium according to claim 4 wherein the gas is air or water vapor and the liquid is water.

6. An article of protective clothing comprising the separatory medium according to claim 5.

7. The article according to claim 6 wherein the protective clothing is selected from the group consisting of space-suits, cleanroom suits, waterproof rainwear, gloves, footwear, socks, undergarments and medical garments.

8. An article of outdoor equipment comprising the separatory medium according to claim 5.

9. The article according to claim 8 wherein the outdoor equipment is a tent or sleeping bag.

* * * * *